(12) United States Patent
Kim et al.

(10) Patent No.: US 7,787,111 B2
(45) Date of Patent: Aug. 31, 2010

(54) SIMULTANEOUS ACQUISITION OF FLUORESCENCE AND REFLECTANCE IMAGING TECHNIQUES WITH A SINGLE IMAGING DEVICE FOR MULTITASK INSPECTION

(75) Inventors: Moon S. Kim, Silver Spring, MD (US); Yud Ren Chen, Laurel, MD (US); Kuanglin Chao, Ellicott City, MD (US); Alan M. Lefcourt, Elkridge, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 128 days.

(21) Appl. No.: 12/109,902

(22) Filed: Apr. 25, 2008

(65) Prior Publication Data

US 2009/0185182 A1    Jul. 23, 2009

Related U.S. Application Data

(60) Provisional application No. 60/907,980, filed on Apr. 25, 2007.

(51) Int. Cl.
*G01N 21/64* (2006.01)

(52) U.S. Cl. .......... 356/73; 356/317; 356/328; 250/461.1; 382/110

(58) Field of Classification Search ............ 356/73
See application file for complete search history.

(56) References Cited

U.S. PATENT DOCUMENTS 6,587,575 B1 *   7/2003   Windham et al. .......... 382/110
6,639,665 B2 * 10/2003   Poole ....................... 356/300

OTHER PUBLICATIONS

Mehl et al., Development of hyperspectral imaging technique for the detection of apple surface defects and contaminations, Journal of Food Engineering, vol. 61, 2004. p. 67-81.*

* cited by examiner

*Primary Examiner*—F. L Evans
(74) *Attorney, Agent, or Firm*—John D. Fado; Robert D. Jones

(57) ABSTRACT

A hyperspectral reflectance and fluorescence line-scan imaging system is used for on-line quality and safety inspection of agricultural commodities. The system simultaneously acquires hyperspectral/multispectral combinations of both fluorescence and reflectance images of the agricultural commodities.

21 Claims, 8 Drawing Sheets a) F530 nm b) F670 nm c) F680 nm a) Mask (660 nm)

b) F660 / F530 c) Binary Image (Detection Results, threshold = 0.99)

a) R600 nm b) R800 nm c) R800 / R750 nm

SIMULTANEOUS ACQUISITION OF FLUORESCENCE AND REFLECTANCE IMAGING TECHNIQUES WITH A SINGLE IMAGING DEVICE FOR MULTITASK INSPECTION

This application claims benefit of U.S. Provisional Application No. 60/907,980, filed 25 Apr. 2007, which is herein incorporated by reference in its entirety.

BACKGROUND OF THE INVENTION

1. Field of the Invention

This invention relates to an online line-scan imaging system capable of simultaneous acquisition of both hyperspectral/multispectral Vis/NIR reflectance and fluorescence images using a single image acquisition device such as for example a Charge Coupled Device (CCD) and to a method of using the system to simultaneously detect and/or inspect (multitasks) a multiple combination of physical, chemical, and biological attributes of products, such as contamination and defects, especially agricultural commodities.

2. Description of the Related Art

The safe production of foods to minimize foodborne illnesses is a concern for both the general public and the entire food industry (Mead et al., Emerging Infectious Diseases, Volume 5, 607-625, 1999). Contamination of food products by animal fecal matter is recognized as a major culprit for pathogenic *E. coli* O157:H7 (Armstrong et al., Epidemiology Rev., Volume 18, 29-51, 1996; Cody et al., Ann. Internal Medicine, Volume 130, 202-209, 1999). Fruits with defects, such as cuts, lesions, and rots that are known to provide favorable ecological niches for bacterial growth are also a safety concern (Mercier and Wilson, Biol. Control, Volume 4, 138-144, 994; Burnett et al., Appl. Environ. Microbiol., Volume 66, 4679-4687, 2000). Opto-electronic imaging techniques as rapid nondestructive sensing tools have been incorporated into agricultural production inspection. Various sensing techniques including the use of X-rays, RGB color, visible/near-infrared (Vis/NIR) reflectance, and fluorescence have been investigated for potential use in online applications (Chen et al., J. Food Process Eng., Volume 21, 351-367 1998; Chen and Tao, Applied Optics, Volume 40 (8), 1195-2000, 2001; Kim et al., 2000(a), J. of Food Engineering, Volume 71 (1), 85-91, 2005; Chao et al., Applied Engineering in Agriculture, Volume 15 (4), 363-369, 1999, Applied Eng. In Agriculture, Volume 20 (5), 683-690, 2004; Mehl et al., J. Food Engin., Volume 61 (1), 67-81, 2004; Liu et al., Applied Spectroscopy, Volume 59 (1), 78-85, 2005; Throop et al., Postharvest Biology and Technology, Volume 36 (3), 281-290, 2005; Yang et al., Trans. ASABE, Volume 49 (1), 245-257, 2006). The most prevalent is reflectance in Vis/NIR portions of the spectrum, used in either monochromatic or multispectral regimes. Optical imaging or machine vision techniques hold great potential for rapid quality and safety inspection of agricultural commodities. In particular, the efficacy of fluorescence imaging for postharvest food safety inspection for fecal contamination has been demonstrated using fruits artificially contaminated with a range of diluted animal feces (Kim et al., Trans. ASAE, Volume 45 (6), 2039-2047, 2002b, Applied Optics, Volume 42 (19), 3927-3934, 2003a, 2005 (supra); Lefcourt et al, Applied Optics, Volume 42 (19), 3935-3943, 2003; Vargas et al., J. of Food Science, Volume 70 (8), E471-E476, 2005).

In the apple processing industry, for example, an online-based machine vision system is typically dedicated to performing a specific sorting task. Current commercial systems address sorting by size, shape and color. The apple industry is in need of sorting methods for apples with defects such as fungal growth, cuts, lesions, bruises, rots, and insect damage. In order to achieve rapid sorting and meet inspection objectives for various quality and safety attributes, multiple machine vision systems may be needed.

SUMMARY OF THE INVENTION

It is therefore an object of the present invention to provide an imaging system for simultaneously capturing a combination of hyperspectral/multispectral reflectance and fluorescence line-scan images of an object using a single image acquisition device such as for example a Charge Coupled Device (CCD).

Another object of the present invention is to provide a line scan imaging system using a single image acquisition device to simultaneously acquire both reflectance and fluorescence image data at selected spectral wavebands.

Another object of the present invention is to provide a line scan imaging system using a single image acquisition device to simultaneously acquire image data with selected spectral bands dedicated to either fluorescence or reflectance imaging and with illumination sources appropriate for the selected imaging wavebands.

Another object of the present invention is to provide a line scan imaging system using a single image acquisition device to simultaneously acquire both reflectance and fluorescence image data at spectral wavebands selected using software reconfiguration.

Another object of the present invention is to provide an imaging system for inspecting and/or detecting a combination of multiple characteristics or artifacts of an object by fusing hyperspectral/multispectral reflectance and fluorescence line-scan image data.

Another object of the present invention is to provide an online hyperspectral reflectance and fluorescence line-scan imaging system to simultaneous inspect for defects and fecal contamination in agricultural commodities.

A further object of the present invention is to provide an apparatus and process which can detect contaminants and defects at a speed which is compatible with the rate at which the agricultural commodity is processed on a production line.

A still further object of the present invention is to provide a real-time automated agricultural commodity inspection system which can quickly and accurately identify defects and fecal contamination.

A still further object of the present invention is to provide a real-time automated agricultural commodity inspection system where wavelengths for reflectance and fluorescence image acquisition can be selected on-the-fly using only software as opposed to hardware changes.

A further object of the present invention is to provide an imaging system that includes an Electron Multiplying Charged-Couple-Device (EMCCD) Imaging Device, a lens assembly, a line-scan spectrograph, a C-mount lens, and a lighting system consisting of a filtered Quartz-tungsten Halogen lamp (QTH) (for NIR reflectance imaging) and a Micro Discharge Lamp (MDL)-High Intensity UV light (for fluorescence imaging).

A further object of the present invention is to provide an imaging system that includes an Electron Multiplying Charged-Couple-Device (EMCCD), a line-scan spectrograph, a C-mount lens and a lighting system consisting of a Quartz-tungsten Halogen lamp (QTH) with a blocking filter to allow reflectance imaging above a selected wavelength (e.g., 700 nm long pass filter) and a Micro Discharge Lamp (MDL)-High Intensity UV light with a second-order blocking filter placed in front of the spectrograph (e.g., 410 nm long pass filter).

A still further object of the present invention is to provide a method for simultaneously detecting defects and fecal contamination on an agricultural commodity by integrating an imaging system of the present invention with a commercial-grade agricultural commodity sorting machine, transporting the agricultural commodity on a conveyer/tray system under a means for capturing an image, capturing an image of said commodity, and processing said image using a means for analyzing spectral imaging data.

A further object of the present invention is to provide a method for simultaneously detecting defects and fecal contamination on an agricultural commodity by integrating an imaging system of the present invention with a commercial-grade agricultural commodity sorting machine, transporting the agricultural commodity on a conveyer/tray system under a means for capturing an image, capturing an image of said commodity, processing said image using a means for analyzing spectral imaging data, and selecting image acquisition wavelengths in real time to optimize detection.

Further objects and advantages of the invention will become apparent from the following description.

BRIEF DESCRIPTION OF THE DRAWINGS

FIG. 1(a) shows a binary masking image obtained using an F670 image FIG. 4(b) shows a representative fluorescence ratio image (approximately 660-530 nm) of samples. FIG. 4 (c) shows a resultant binary image for feces-contaminated spots. Binary images for fecal contamination were obtained by the application of a simple thresholding method with a global threshold value of approximately 0.99.

FIG. 6 (a) shows representative reflectance images in the visible region at approximately 600 nm. FIG. 6 (b) shows representative reflectance images in the NIR region at approximately 800 nm. FIG. 6 (c) shows two NIR reflectance ratio images at 800 nm/750 nm.

DETAILED DESCRIPTION OF THE INVENTION

A single inspection system needs to have a combination of (1) flexibility in employing sensing techniques, e.g., fluorescence and reflectance, (2) selectivity of multispectral bands, and (3) capabilities of simultaneous acquisition of multispectral bands. The present invention is a rapid online line-scan imaging system capable of both hyperspectral/multispectral and fluorescence imaging. Recent advancements for sensitive low-light imaging devices and peripherals allow hyperspectral imaging of fast moving targets. Though redundant in spectral data, the online line-scan system provides a range of spectral data to evaluate inspection of agricultural commodities for a variety of quality and safety attributes. The system of the present invention meets the needs of the agricultural commodities assessing industry to achieve rapid online safety, such as fecal contamination known to be the major source of pathogens, and quality assessments. Reflectance imaging at multiple wavelengths is needed to detect quality issues, while fluorescence imaging at multiple wavelengths is needed to detect fecal contamination on agricultural commodities. There are no online inspection systems for detection of animal fecal contamination on fruits and vegetables. The present invention allows selections of numerous combinations of multispectral parameters of both fluorescence and reflectance methods that can be used to simultaneously sort agricultural commodities based on desired characteristics such as, defects, shape, size, color, color variation, and the presence of fecal contamination. The present invention simultaneously acquires hyperspectral/multispectral combinations of both fluorescence and reflectance images of the objects. The wavelengths for fluorescence (530 nm and 660 nm for apple safety inspection) and reflectance (750 nm and 800 nm for apple quality inspection) do not overlap. It can be readily configured to acquire only a few selected spectral channels (in multispectral or random track mode), providing additional potential to meet other sorting requirements such as shape and other quality attributes.

The present invention is an economically viable solution which significantly reduces the cost and complexity of existing systems based on multiple imagers, and/or inspection stations such as, for example, a sorting system for color/size and an additional system with multiple imagers for defects with an added benefit of inspection for fecal contamination.

Figure 1:
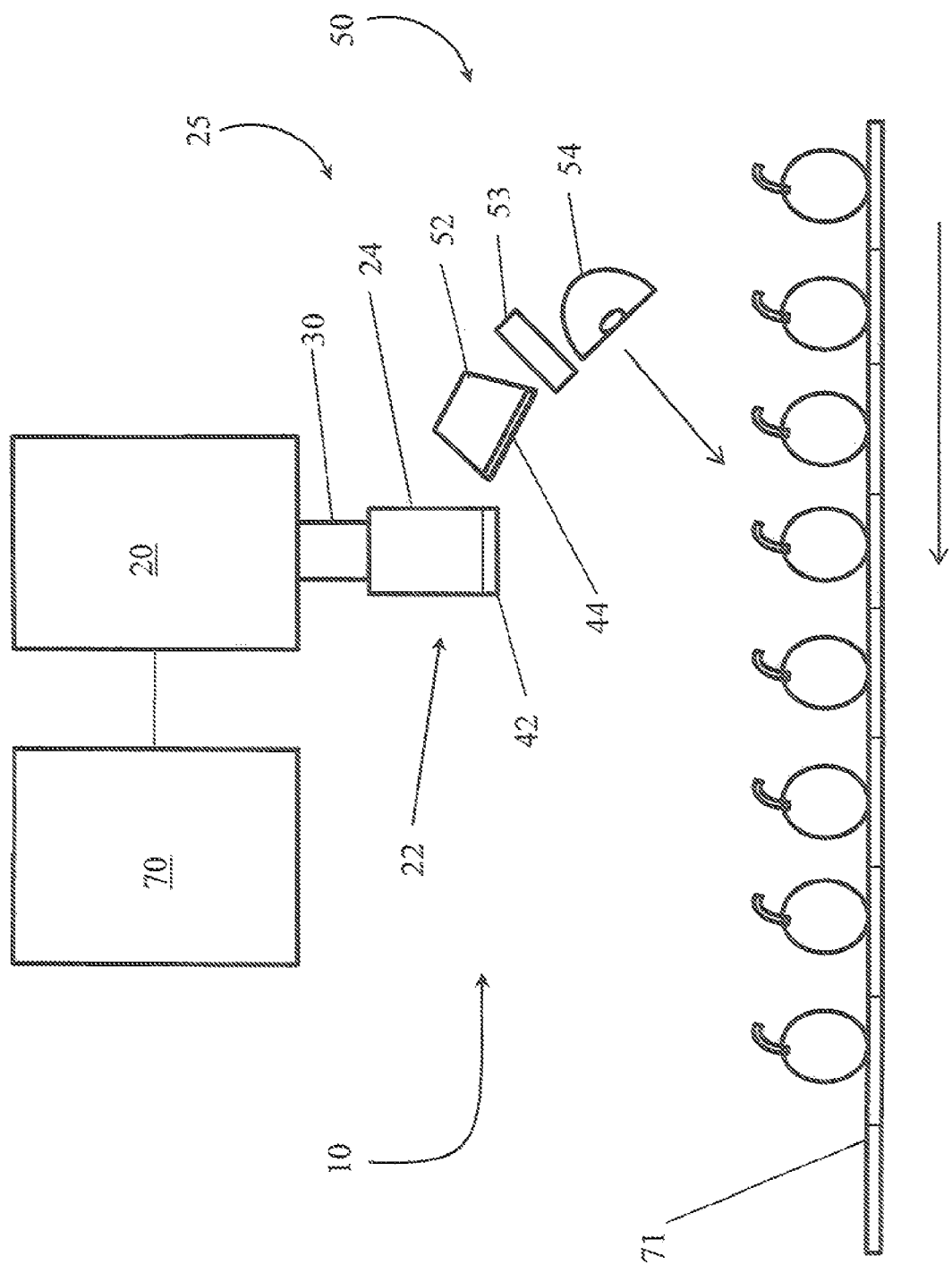
FIG. 1 is a schematic drawing of the online hyperspectral reflectance and fluorescence line scan imaging system disposed above a commercial apple conveyance and sorting machine.

Imaging system 10 (FIG. 1) of the present invention includes a means for obtaining spectral images 25, a lighting system 50, and a data processing unit 70. One embodiment of the present invention includes a hyperspectral imaging system 10 (FIG. 1). Hyperspectral imaging device 10 includes at least a means for obtaining spectral images 25, such as a single image acquisition device such as for example a Charge Coupled Device (CCD), and more specifically an Electron Multiplying Charged-Couple-Device (EMCCD Imaging Device 20 PhotoMAX Roper Scientific, Inc., Trenton, NJ, USA; iXon and Luca, Andor Technology Limited, CT.), lighting system 50, and data processing unit 70. The means for collecting spectral images 25 for purposes of this embodiment, includes an Electron Multiplying Charged-Couple-Device (EMCCD) Imaging Device 20, a lens assembly 22 including a line-scan spectrograph 30 and an optical lens 24. Line-scan spectrograph 30 has a nominal spectral range of from about 400 nm to about 1000 nm and attaches to imaging device 20 for generating line-scan images. Lens assembly 22 includes a c-mount lens 24, such as for example, a Xenoplan (Scheider, Haugppauge, N.Y.), Nikkor (Nikon Inc., Melville, N.Y.) and attaches to line-scan spectrograph 30. The data acquisition/processing unit 70 is operatively connected to the means for obtaining hyperspectral/multispectral images 25.

Lighting system 50 includes a Quartz-tungsten Halogen lamp (QTH) 52 (reflectance lamp). NIR LEDs or a NIR laser without the long pass filter can also be used as a reflectance lamp. The lighting system also includes a Micro Discharge Lamp (MDL)-High Intensity UV light 54. LEDs, a laser, or a pressurized vapor lamp can also be used for fluorescence excitation. The system further includes two long pass filters (approximately 410 nm and 700 nm) 42 and 44. Filter 42 is to eliminate second order of the UV-A fluorescence excitation light in the NIR portion on the spectrograph by placing a second-orderblocking filter (i.e., fluorescence excitation=320 to 400 nm, then second order starts to shows up at 640 nm and ends at 800 nm). For a QTH lamp, filter 44 is to eliminate light where fluorescence is measured. To measure reflectance band (s), additional monochromatic light(s) in the visible, such as a red laser for reflectance in the red (e.g., 630 nm), can be added. Long pass filter 42 is operatively placed in front of the C-mount lens 24 and long pass filter 44 is operatively placed in front of halogen lamp 52.

Imaging Device 20 has approximately 512×512 pixels and is thermoelectrically cooled down to approximately −70 degrees centigrade via a three-stage Peltier device. The imaging device is coupled with an approximately 10 MHz to 30 MHz (pixel read-out rate), 14-bit and/or 16-bit digitizer 22. An imaging spectrograph 30 (ImSpector V10, Spectral Imaging Ltd., Oulu, Finland) and a C-mount lens 40 (Rainbow CCTV S6×11, International Space Optics, S.A., Irvine, Calif., USA) are attached to EMCCD Imaging Device 20. The instantaneous field of view (IFOV) is limited to a thin line by the spectrograph aperture slit of approximately 50 microns. Through the slit, light from the scanned IFOV line is dispersed by a prism-grating-prism line-scan spectrograph and projected onto EMCCD Imaging Device 20. Therefore, for each line-scan, a two-dimensional (spatial and spectral) image is created with the spatial dimension along the horizontal axis and the spectral dimension along the vertical axis of the EMCCD Imaging Device 20.

Interface software (WinViedw.32 cersion 2.5.19.0) provided by the EMCCD Imaging Device 20 manufacturer was used for data acquisition. To increase the imaging speed and to minimize the redundancy in the spectral imaging data, the original image size, approximately 512×512 pixels, was reduced using an approximately 6×6 binning to produce an image size of approximately 85×85 pixels. The approximately 6×6 binning and the apple-sorting machine speed of slightly greater than 3 apples per second resulted in a spatial pixel resolution of approximately 2 mm². It should be noted that not all EMCCD imaging device 20 pixels in the spectral (vertical) dimension were utilized; the light dispersed b the spectrograph did not span the full vertical width of the EMCCD imaging device 20. Thus, the effective spectral dimension was further reduced to approximately 60 pixels (channels) spanning from approximately 400 to approximately 1000 nm with a channel interval of approximately 10 nm. See Kim et al., Trans. ASAE, Volume 44(3), 721-729, 2001 (herein incorporated by reference in its entirety) for a detailed description of spectral calibration.

In one embodiment of the present invention, the line-scan imaging system 10 uses two different independent continuous wave (CW) light sources: (1) a pair of 150-w quartz halogen lamps 50 for reflectance imaging and a micro-discharge high intensity UV lamp 60 with a diffuse filter 42 (ML-3500, Spectronics Corp., Westbury, N.Y., USA) for fluorescence imaging. Reflectance at wavelengths shorter than approximately 450 nm was not used due to poor signal-to-noise ratio; the very low irradiance in that portion of the spectrum was an attribute of the of the quartz halogen light sources. With UV-A illumination, most biological materials exhibit fluorescence emissions between approximately 400-700 nm. Thus, fluorescence spectra are present only in that spectral range.

Image processing and analysis software was developed on a Microsoft (MS) Visual Basic (Version 6) platform in the MS Windows operating system. Using the downloaded hyperspectral image cube data captured via an A/D board, the software captures and allows visualization of individual apple images and automated detection of feces-contaminated spots and defects as the stream of hyperspectral image cube data are accessed. System 10 data acquisition function is incorporated into software to achieve real-time visualization and detection.

Using apples as a model for the system, a preliminary test suggests that over 50 apples per second could be processed using a computer with a 2 GHz processor. For system 10, increasing the data transfer rate, i.e., from approximately 10 MHz to approximately 30 MHz pixel readout rate, allows agricultural commodities moving at even higher speeds to be detected, and/or significantly improve the spatial image resolution.

The line speed of sorting machine 71 is adjusted to run at a desired speed. For apples, for example, the speed is set to run at approximately slightly higher than 3 apples/second.

Figure 8:
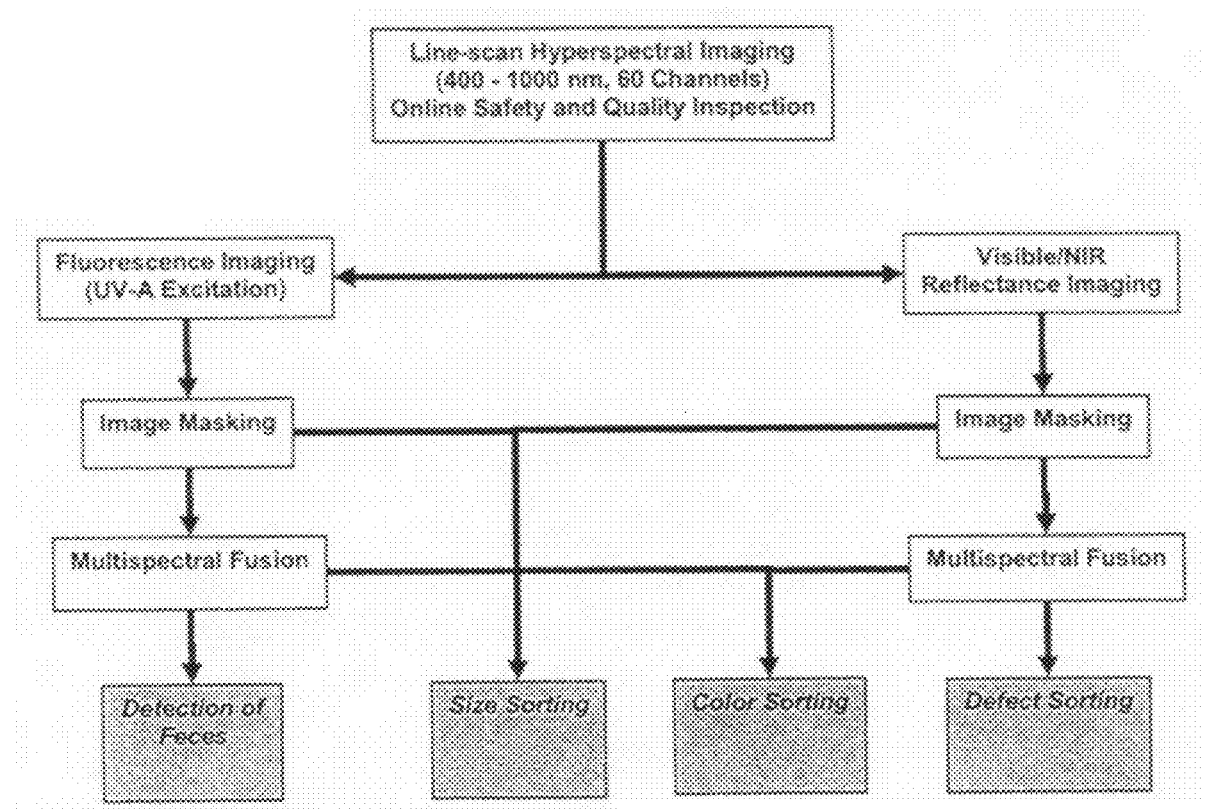
FIG. 8 is a flowchart showing the application of using both reflectance and fluorescence in a method for quality and safety inspection/sorting of apples.

The imaging system is operated in multispectral mode to capture fluorescence at 530 and 660 nm for fecal contamination and reflectance at 750 and 800 nm for defects (FIG. 8). In addition, a red laser (HeNe laser) 53 for reflectance in the red (e.g., 632 nm) can be added to acquire reflectance in the red band which is used to determine red coloration of apples. Masking provides the total number of image pixels occupied by an apple, which is the measure of size. These sorting parameters are determined while apples are in transition to sorters.

The following examples are intended only to further illustrate then invention and are not intended to limit the scope of the invention which is defined by the claims. Apples are used as a model for the system of the present invention.

EXAMPLE 1

Hyperspectral line-scan imaging system 10 integrated with a commercial apple-sorting machine was used to detect apples for fecal contamination and defects at a processing line speed of over three apples per second. A batch of over 500 'Golden Delicious' apples originally intended for making unpasteurized apple cider and a second batch of over 500 'Golden Delicious' apples were obtained from a local orchard. The cider apples had been presorted by the orchard and included fruits with defects such as fungal infections (black pox and sooty blotch), bruises, cuts, lesions, and insect damage. The second batch contained normal apples exhibiting minimal blemishes and had been destined for fresh consumption.

Fresh cow feces of animals that had been fed feedstuffs containing green roughage, were collected from the USDA farm facilities in Beltsville, Md. A thin cow feces spot of approximately 2 cm in diameter, was artificially created on each cider apple by smearing the cow feces on the apple using a spatula. Note that the smears of cow feces created transparent film-like coatings on the apples and, visually, were not easily discernable by human eye. A total of 60 cider apples were selected for treatment with cow feces but only 59 were actually treated, 1 apple was mistakenly left out.

Because the potential for contamination increases with the presence of defects such as cuts and lesions that present favorable ecological niches for bacterial growth (Mercier and Wilson, 1994 supra; Burnett et al., 2000, supra), the fecal contamination treatment was applied only to cider apples exhibiting defects. Online fluorescence images were acquired for 60 apples with defects prior to feces treatment, for the 59 feces-treated apples one day after the feces treatment, and again for the 59 feces-treated apples one month after cold storage. An additional 79 normal apples were also imaged as control samples, before and after one month of cold storage. For the fecal contamination inspection study, the total number of apple images used was 257, consisting of 118 fecal-contaminated apple images and 139 control apple images.

For defect detection, a total of 179 defects were imaged. The 59 cider apples that had been treated with fecal smears were included among the 179 images of apple defects. Previous studies have shown that a thin transparent smear of cow feces could not be readily detected with reflectance imaging methods in the visible/NIR regions of the spectrum (See Kim et al., Trans. ASAE, Volume 45 (6), 2027-2037, 2002a). In addition, 196 normal apples with minimal blemishes were imaged as control samples.

Apples were selected randomly from the respective batches with no consideration for a specific defect type. Based on visual observation, the defect samples appeared to encompass a variety of defect types and a range of degrees of defects. Individual feces-treated apples were purposely oriented on the sorting machine trays with the fecal smear spots facing the camera 20 while control apples were randomly positioned on the trays by the loading mechanism of the sorting machine.

Figure 2:
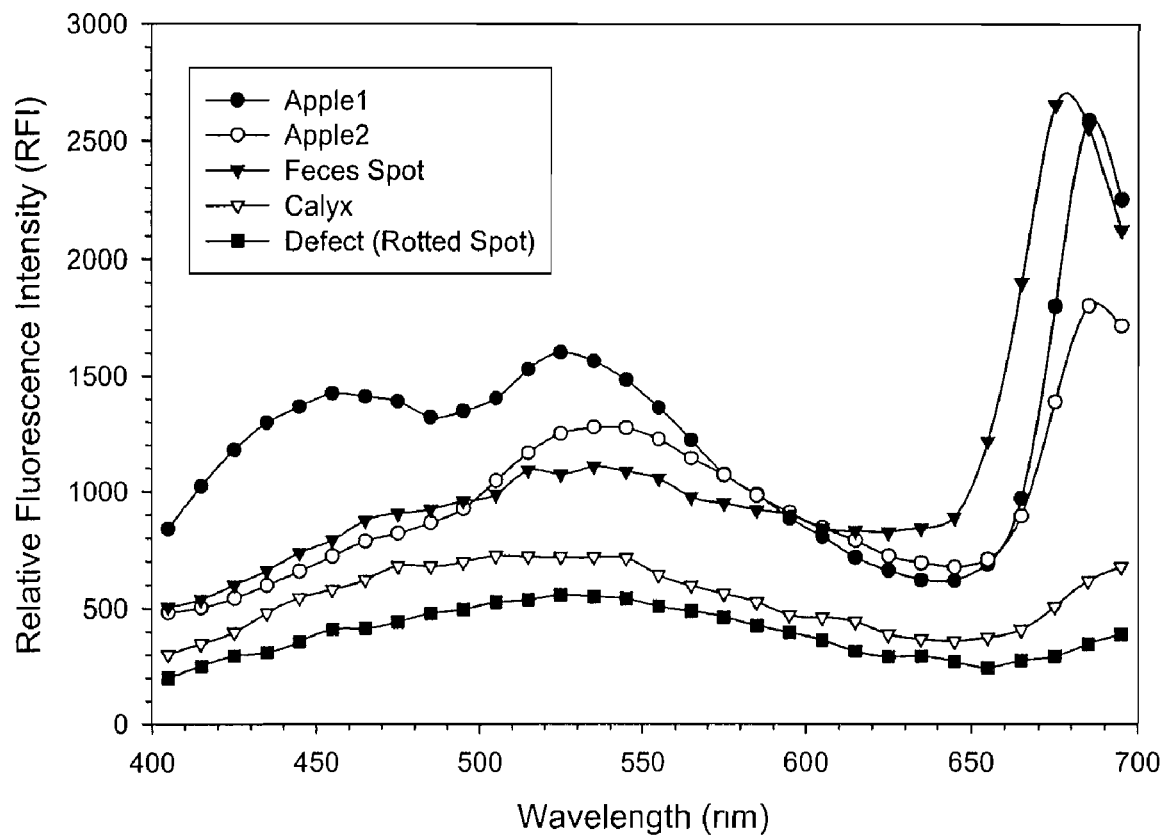
FIG. 2 is a graph showing the representative fluorescence spectra acquired using the online hyperspectral line-scan imaging system.

Representative fluorescence spectra from approximately 400 to approximately 700 nm were extracted from areas of hyperspectral images of two normal apples surfaces, a feces spot, a calyx region (shaded) and a rotted (defect) portion of an apple (FIG. 2). Note that the individual spectra were obtained from individual regions of interest consisting of approximately 4-9 pixels each (averaged intensity per wavelength). With UV-A excitation, Golden Delicious apples typically exhibit a broad emission in the blue and green regions of the spectrum with maxima located approximately at 460 and approximately at 530 nm, respectively. Chlorophyll a fluorescence with emission maximum at near approximately 680 nm is also observed from Golden Delicious apples. For the areas of apples coated with the transparent fecal smears, a blue shift in the chlorophyll a emission peak, e.g. approximately 670 nm, is typically observed (Kim et al., J. of Food Protection, Volume 66 (7), 1198-1207, 2003b).

Relative intensity variations dependent upon degree of fruit ripeness were observed. Furthermore, the relative intensity differences were wavelength dependent in that blue and red emissions compared to the green band for a well-ripened apple (Apple2) were lower than for a green apple (Apple1) (FIG. 2). The rotted spot and calyx region showed a broad and relatively low blue-green fluorescence and minimal chlorophyll a emission compared to the emissions of the greenish Golden Delicious apples. Responses of stem and adjacent shaded regions were also similar to those of calyx and rotted spots (Figure not shown).

Figure 3:
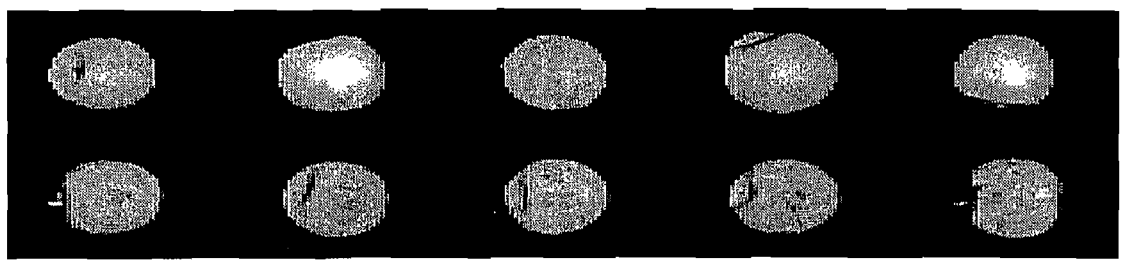
FIGS. 3(a)-(c) are photographs showing fluorescence images at FIG. 3(a) approximately 530 nm, FIG. 3(b) approximately 670 nm, and FIG. 3(c) approximately 680 nm. Images were acquired with an apple-sorting machine with a line speed of three apples per second.
Figure 3:
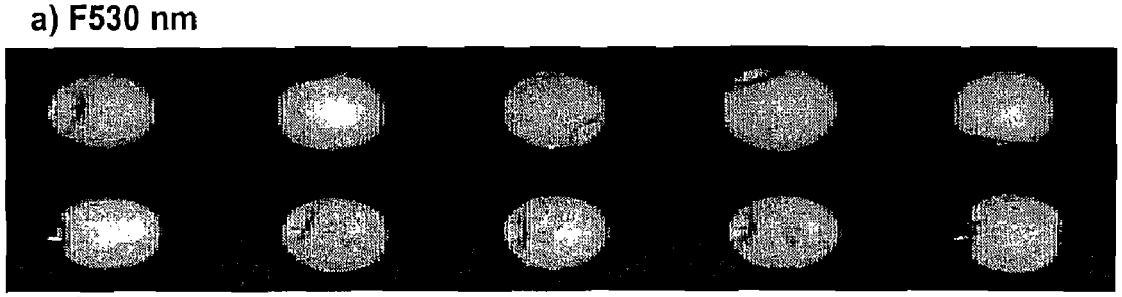
Figure 3:
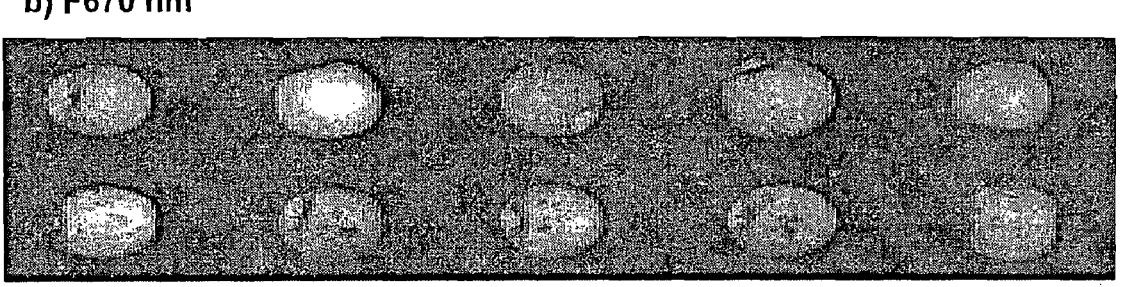

FIG. 3 shows fluorescence emission band images of representative samples at the approximately 530 nm emission maximum in the green region (F530), at the approximately 670 nm emission peak for bovine feces (F670), and at the approximately 680 nm chlorophyll a emission peak (F680). In each of the three emission band images, normal apples (with minimal defects) are in the top row, while feces-treated defect apples, i.e., those exhibiting bruises and cuts, rotted areas, and fungal growths such as sooty blotch, are in the bottom row. The normal apples were imaged with apples randomly oriented by the sorting machine, while the feces-treated apples were positioned by hand to ensure that the fecal spots faced the camera. The imaging parameters used in this example, such as pixel readout rate and binning, and the sorting-line speed, resulted in approximately 900 pixels for a single apple image.

The fluorescence images show the defects and some stems as relatively dark spots compared to the surrounding normal apple surfaces. It is apparent that the concave features of the stem and calyx regions of the apples resulted in some shaded regions that were sometimes observed as relatively darker spots, depending on the orientation of the apples. Apple-to-apple intensity variation was also observed for the emission regions in this example and was attributed to individual color and/or maturity differences.

The inventors have previously found a two-fluorescence band ratio to be an efficient multispectral image fusion method for detection of fecal contamination on apples (Kim et al., 2002b, supra, 2005, supra). Compared to normal apple surfaces, feces spots have relatively lower and higher emission in the green and red (the blue-shift feces) wavelength regions, respectively, and thus a ratio of these two bands enhances the appearance of the fecal spots on apples. For calyx and rotted spots, green fluorescence responses compared to the fecal emission maximum in the red were relatively higher, and the ratio of the two bands yielded much smaller values than those for feces spots. Two-band ratio also reduced the spatial heterogeneity of normal apple surfaces, especially using a more blue-shifted red fluorescence band, e.g., approximately 660 nm.

Figure 4:
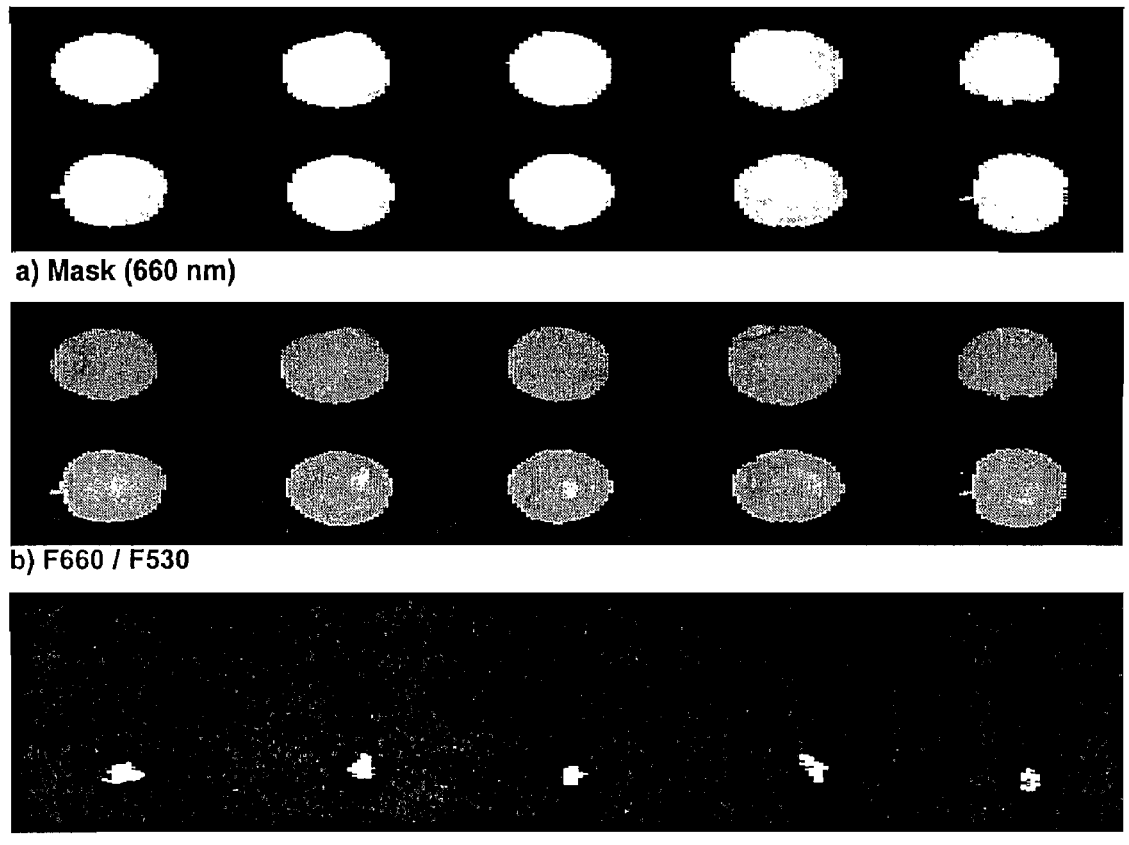
FIG. 4 (a)-(c) are photographs showing.
Figure 5:
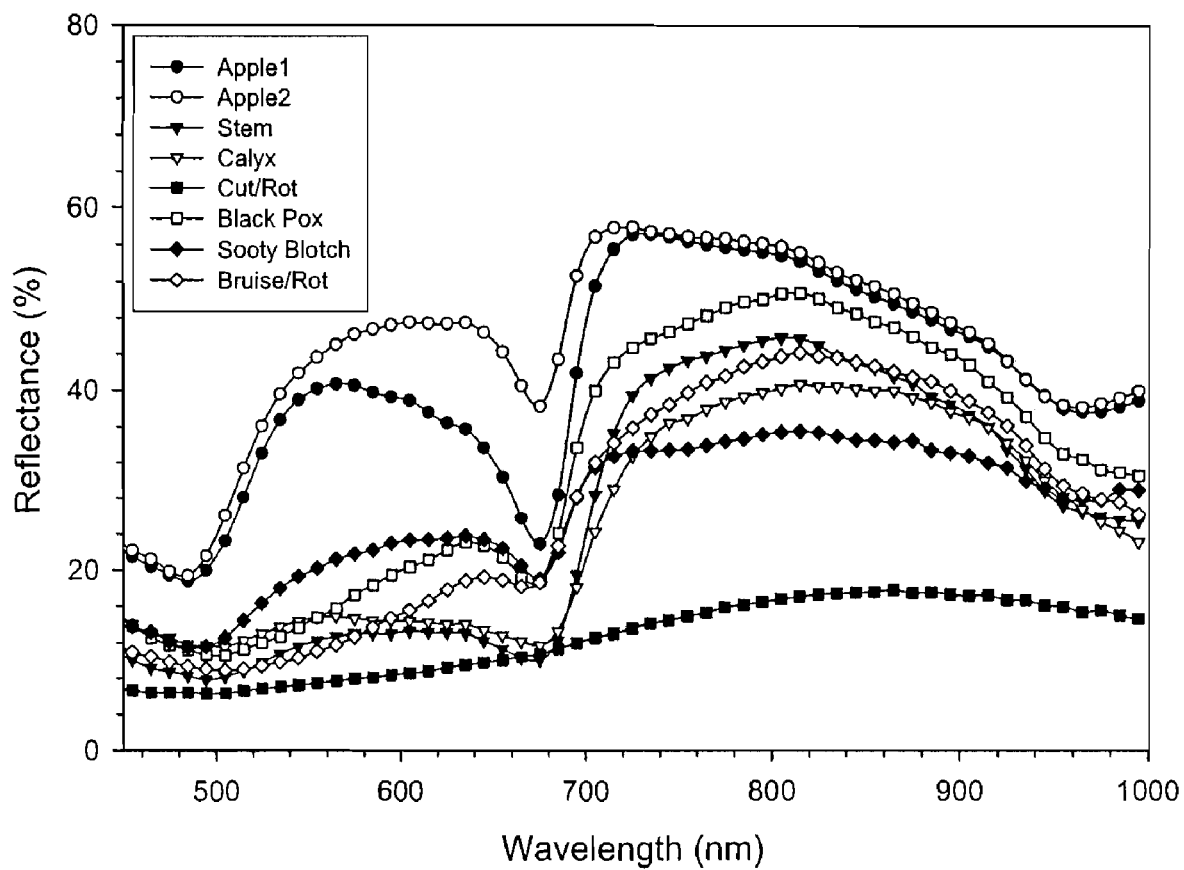
FIG. 5 is a graph showing representative reflectance spectra using the online hyperspectral line-scan imaging system.

Prior to calculating the ratio values of the two-banded images, a masking operation was performed to eliminate background portions of the images. FIG. 4a shows a mask image for the apples in FIG. 3 that was created using the F660 band with a single threshold value (RF of approximately 330). FIG. 4b shows the ratio image of approximately 660 nm over approximately 530 nm (F660/F530). Feces-treated spots that previously were not clearly visible in the individual emission images appear as brighter, more distinct regions for the bottom row apples in the ratio image. In addition, the feces spots are brighter than the surrounding apple surfaces regardless of the presence of defects, fungal spots, and stem and calyx regions, including the shaded regions. FIG. 4c shows the binary image highlighting the regions of feces contamination, obtained by subjecting the ratio image to a simple thresholding method using a global threshold value of approximately 0.99. Pixels in the image with intensity values less than or equal to the threshold value are assigned to 0 (or black) [and 1 (or white) for pixels with the values greater then the threshold]. Based on the samples in this example, up to a 100% detection rate (118 feces-treated apples) was achieved, with no false positives (0 out of 19 normal apples). Fluorescence imaging techniques have consistently demonstrated very high detection rates for detecting animal fecal contamination on apples. The representative reflectance spectra from approximately 450 to approximately 1000 nm extracted from areas of hyperspectral images for normal apples are shown in FIG. 5. As for the fluorescence spectra shown in FIG. 2, each individual reflectance spectrum represents a region of interest consisting of approximately 4-9 pixels (averaged intensity per wavelength). Reflectance of Golden Delicious apples exhibited relatively high green reflectance at around 550 nm due to the green coloration, as well as a characteristic absorption of chlorophyll a in the red region of the spectrum with absorption maximum at around 670 nm.

Differences in the apples' natural green coloration affected reflectance responses in the green and red regions, see for example Apple1 and Apple2 in FIG. 5. The reflectance spectra of defects in rotted and fungal growth regions, although visually black in appearance, also exhibited varying degrees of the characteristic feature reminiscent of chlorophyll a absorption in the red region. The spectral reflectance responses were consistent in that the NIR slope between approximately 750 and approximately 800 nm was negative for the normal apples and positive for the defects.

Figure 6:
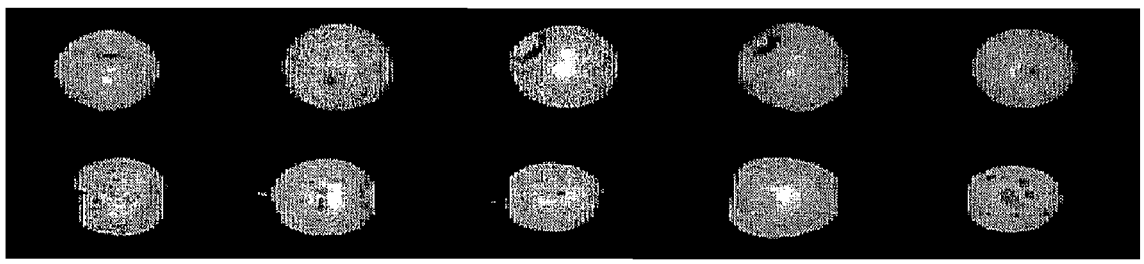
FIGS. 6 (a) to 6(c) are photographs showing.
Figure 6:
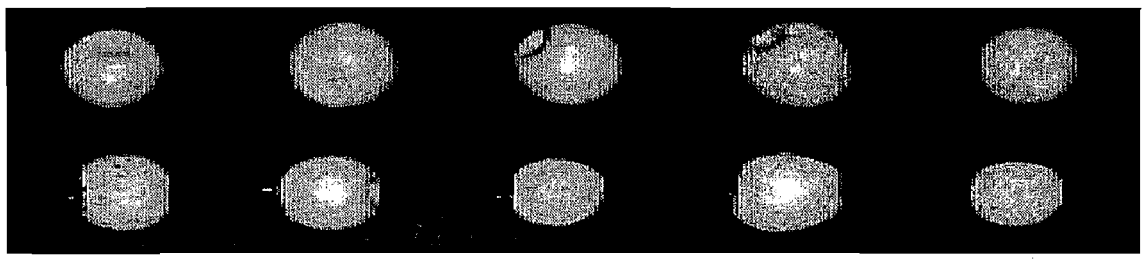
Figure 6:
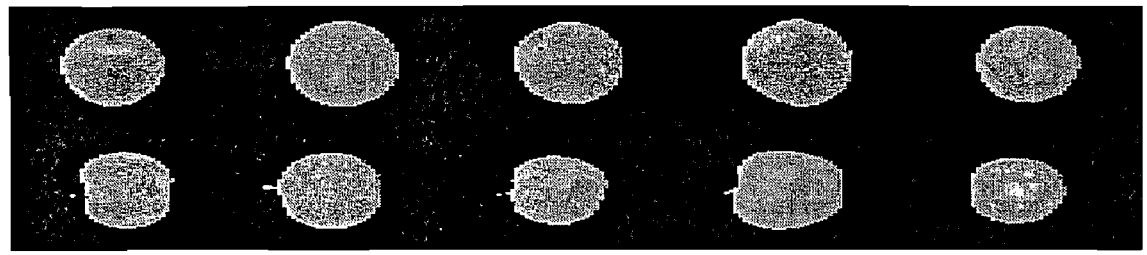

The reflectance images at approximately 600 nm (R600) and approximately 800 nm (R800) in FIGS. 6a and 6b, respectively, show representative normal apples in each top row and feces-treated defect apples in each bottom row. Note that these apples are different samples from those shown in the fluorescence images in FIG. 4. The defect portions and the stem/calyx regions and shaded areas of the samples exhibited relatively darker reflectance than the surrounding normal apple surfaces in the wavelength regions under investigation. Based on the spectral responses, a NIR two-band ratio using approximately 750 nm and approximately 800 nm band pair may provide the greatest difference in ratio values between normal apple surfaces and defect p\portions (FIG. 6c). However, because of the spectral resemblance of apple stem and calyx regions to defects including rots, cuts, lesions, and fungal growth, false positives are ever present as evidenced in FIG. 6c.

Because of the use of a grating in the spectrograph, a second-order effect is present in the longer wavelength region starting at approximately 800 nm. One of the considerations in selection of suitable bands in terms of multispectral band fusion is that the focal length (plane) of a camera lens is wavelength dependent. To minimize artifacts it is preferable to select two wavelengths with close proximity without overlapping spectral regions. Based on the spectral characteristics of various apple surface conditions, two NIR bands at approximately 750 nm and approximately 80 nm, separated by only approximately 50 nm, were chosen.

Figure 7:
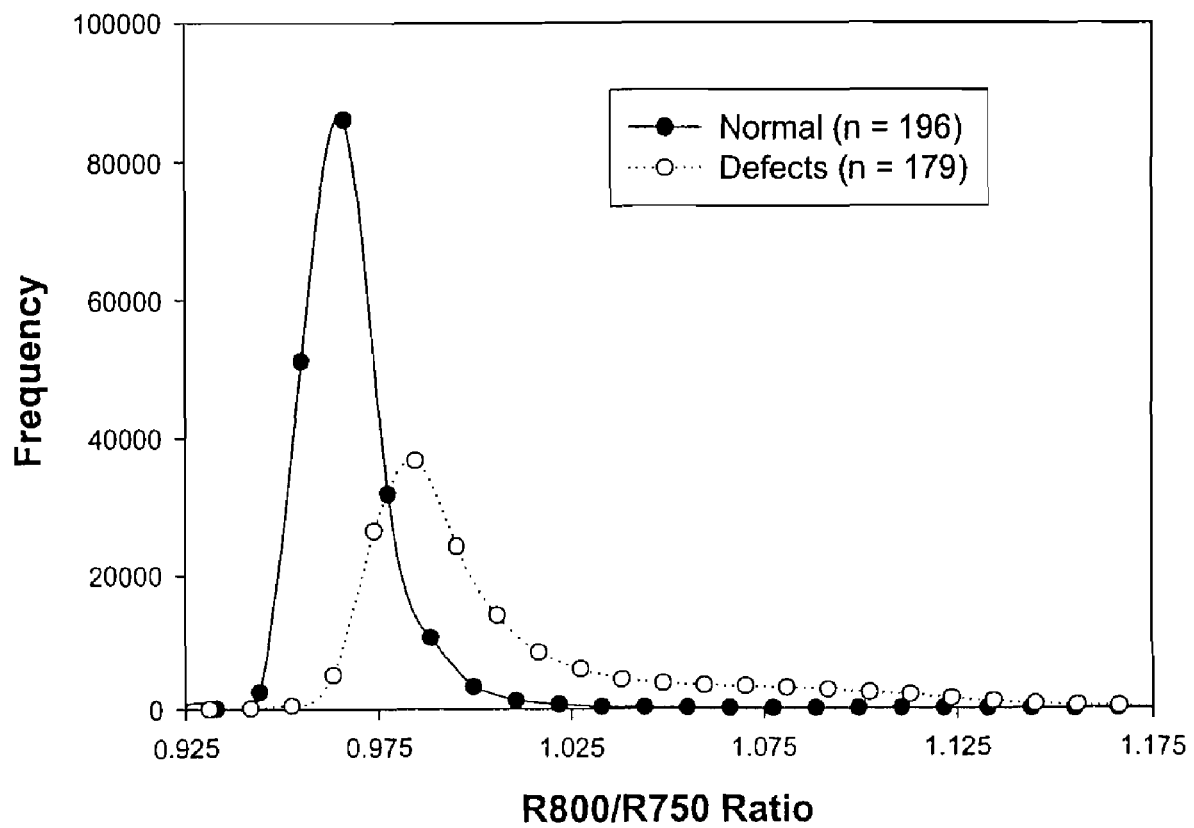
FIG. 7 is a graph showing a pixel intensity histogram from the 800/750 nm NIR ratio for normal and defect apples.

As suggested by Kim et al. (2002a), utilizing morphological image processing to eliminate false positives emanating from the stem/calyx regions would be computationally costly. Having knowledge of the location of calyx or stem in the image would be beneficial in morphologically based defect detection (Narayanan et al., 2006). With the use of the NIR reflectance ratio image (FIG. 6c), it is recognized that the ratio means and standard deviations for normal apples were significantly lower than for apples with defects, regardless of the presence of stem/calyx false positives (FIG. 7). In addition to the presence of the stem and/or calyx, the presence of defects increased the mean ratio values and the spatial heterogeneity of the NIR ratio responses. Thus, the means and coefficients of variation of the ratio values, as a simple classification model input, were calculated for individual apples and subjected to SAS discriminant analysis (SAS version 8.0, Cary, N.C.; PROC DISCIM, linear model with one-cross out validation). This resulted in the correct classification of approximately 98% of normal apples, 4 out of 196 misclassified, and 99.4% of defects, 1 out of 179 misclassified. The misclassification of some normal apples as defects might be attributed to those apples actually having some very minor defects/blemishes.

The foregoing detailed description is for the purpose of illustration. Such detail is solely for that purpose and those skilled in the art can make variations without departing from the spirit and scope of the invention.

We claim:

1. An imaging system for simultaneously capturing a combination of hyperspectral/multispectral reflectance and fluorescence images of an object, the system comprising:
   a charge coupled device (CCD) and associated data processing unit;
   a spectrograph in communication with the CCD,
   a reflectance lamp illuminating the object; and,
   an ultraviolet light illuminating the object;
   wherein as the object passes through a field of view of the spectrograph, the object is simultaneously illuminated by the reflectance lamp and the ultraviolet light so that an image is acquired by the spectrograph and projected into the CCD, thereby enabling the CCD to simultaneously capture the object fluorescence and reflectance in the image, and enabling the data processing unit to process both florescence image data and reflectance image data.

2. The imaging system of claim 1 wherein the CCD is an electron multiplying CCD.

3. The imaging system of claim 1 further comprising a lens assembly connected to the spectrograph.

4. The imaging system of claim 3 wherein the lens assembly comprises a c-mount lens.

5. The imaging system of claim 4 further comprising an ultraviolet blocking filter attached to the c-mount lens so that the ultraviolet blocking filter blocks light at wavelengths narrower than 410 nm.

6. The imaging system of claim 1 wherein the spectrograph comprises a dispersive imaging line-scan spectrograph.

7. The imaging system of claim 1 wherein the reflectance lamp comprises a quartz-tungsten halogen lamp.

8. The imaging system of claim 7 wherein a long pass filter is positioned in front of the reflectance lamp so that the long pass filter blocks light at wavelengths narrower than 700 nm.

9. The imaging system of claim 1 wherein the ultraviolet light comprises a micro discharge high intensity ultraviolet light.

10. The imaging system of claim 1 wherein the system simultaneously captures fluorescence between 400 nm and 700 nm, and reflectance between 700 and 1000 nm.

11. The imaging system of claim 1 wherein the system allows the use of a HeNe laser for reflectance at 632 nm in a red color range.

12. The imaging system of claim 1 wherein the system simultaneously captures fluorescence at 530 and 660 nm wavelengths, and reflectance at 750 and 800 nm wavelengths.

13. The imaging system of claim 1 wherein the system eliminates reflectance responses in the wavelength regions where fluorescence responses occur.

14. The imaging system of claim 1 wherein the data processing unit is operatively connected to a sorting machine so that the sorting machine makes object sorting selections based on data provided by the data processing unit.

15. An imaging system for collecting florescence and reflectance data comprising
   a charge couple device;
   a data processing unit;
   a spectrograph;
   a reflectance lamp; and
   an ultraviolet light;
   wherein the spectrograph simultaneously projects fluorescence and reflectance data into the charged couple device for processing by the data processing unit.

16. The imaging system of claim 15 further comprising a sorting machine that makes sorting decisions based on information from the data processing unit.

17. The imaging system of claim 15 wherein the charge couple device is an electron multiplying charge couple device.

18. A method of capturing a combination of hyperspectral/multispectral reflectance and fluorescence images of selected objects, the method comprising the steps of:
   (a) providing a charge couple device (CCD) and an associated data processing unit;

(b) connecting a spectrograph with the CCD so that the CCD is in communication with the spectrograph and one of the selected objects is within a field of view of the spectrograph;

(c) illuminating the each of the selected objects with a reflectance lamp; and, (d) illuminating the each of the selected objects with an ultraviolet light;

(e) using the spectrograph to obtain an image of each of the selected objects as the objects are simultaneously illuminated by the reflectance lamp and the ultraviolet light;

(f) projecting the image obtained by the spectrograph into the CCD, thereby enabling the CCD to capture the image and allowing the data processing unit to process both florescence data and reflectance data associated with the image.

19. The method of claim 18 wherein the CCD is an electron multiplying CCD.

20. The method of claim 18 further comprising communicating processed image data to a sorting machine so that the sorting machine can sort the objects based on processed image data.

21. The method of claim 18 further comprising eliminating reflectance responses in the wavelength regions where fluorescence responses occur.

* * * * *